United States Patent [19]

Hulme

[11] 4,120,912

[45] Oct. 17, 1978

[54] RECOVERY OF LEWIS ACID/BRONSTED ACID CATALYST WITH HYDROGEN AT ELEVATED TEMPERATURES AND PRESSURES

[75] Inventor: Roger Hulme, Somerville, N.J.

[73] Assignee: Exxon Research & Engineering Co., Linden, N.J.

[21] Appl. No.: 812,635

[22] Filed: Jul. 5, 1977

Related U.S. Application Data

[63] Continuation-in-part of Ser. No. 628,589, Nov. 4, 1975, abandoned.

[51] Int. Cl.$^2$ .......................... C07C 3/54; C07C 3/56; C07C 5/28
[52] U.S. Cl. .......................... 260/683.47; 260/683.68; 260/666 P; 260/671 R
[58] Field of Search ........... 260/683.47, 666 P, 671 R, 260/683.68, 683.67; 252/411 R

[56] References Cited

U.S. PATENT DOCUMENTS

| | | | |
|---|---|---|---|
| 2,727,010 | 12/1955 | Zimmerschied | 252/411 R |
| 3,352,941 | 11/1967 | Schoen et al. | 252/411 R |

*Primary Examiner*—George Crasanakis
*Attorney, Agent, or Firm*—John W. Ditsler

[57] ABSTRACT

Deactivated or partially deactivated hydrocarbon conversion catalysts comprising (a) one or more Lewis acids selected from the group consisting of the fluorides, chlorides and bromides of boron(III), titanium(IV), zirconium(IV), hafnium(IV), phosphorus(V), arsenic(V), tantalum(V), niobium(V) and mixtures thereof and (b) a strong Bronsted acid, may be recovered by contacting said catalysts with hydrogen at elevated temperatures and pressures. The preferred Lewis acid is an acidic halide, preferably tantalum pentafluoride, niobium pentafluoride or mixtures thereof. The preferred Bronsted acid is a hydrogen halide, preferably hydrogen fluoride.

27 Claims, No Drawings

RECOVERY OF LEWIS ACID/BRONSTED ACID CATALYST WITH HYDROGEN AT ELEVATED TEMPERATURES AND PRESSURES

CROSS REFERENCE TO RELATED APPLICATIONS

This is a continuation-in-part of application Ser. No. 628,589, filed Nov. 4, 1975, now abandoned.

BACKGROUND OF THE INVENTION

1. Field of the Invention

The present invention relates to a process for regenerating a catalyst of the type used in hydrocarbon conversion processes. More particularly, this invention relates to a process for regenerating a catalyst that has become deactivated or partially deactivated by the formation of stable, catalytically inert, complexes during contact with a hydrocarbon feedstock, said catalyst comprising (a) one or more Lewis acids selected from the group consisting of the fluorides, chlorides and bromides of boron(III), titanium(IV), zirconium(IV), hafnium(IV), hafnium(IV), phosphorus(V), arsenic(V), tantalum(V), niobium(V) and mixtures thereof and (b) a strong Bronsted acid, by contacting said catalyst with hydrogen at elevated temperatures and pressures.

2. Description of the Prior Art

It is well known in the prior art that the activity of Friedel-Craft's type hydrocarbon conversion catalysts declines gradually due to the accumulation of various contaminants or poisons, such as compounds of carbon, sulfur, nitrogen, oxygen, metals, water and the like, until the catalysts cease to exhibit an economic activity. In such cases, depending upon economic factors, the catalyst may be replaced or regenerated to restore desired activity levels.

Several methods have been suggested in the prior art for regenerating Friedel-Craft's type hydrocabon conversion catalysts via hydrogenation. For example, U.S. Pat. No. 3,173,881 teaches the reactivation of an aluminum halidehydrocarbon sludge by using hydrogen at elevated temperatures and pressures, preferably in the presence of a hydrogen halide. In addition, U.S. Pat. No. 3,352,941 teaches the regeneration of an aluminum halide supported catalyst with hydrogen at elevated temperatures and pressures wherein the hydrogen gas preferably includes a hydrogen halide corresponding to the particular aluminum halide used. Nonetheless, it is believed that none of the foregoing prior art discloses a method for regenerating the catalyst systems described hereinafter with hydrogen.

SUMMARY OF THE INVENTION

Now in accordance with the present invention, it has been discovered that a deactivated or partially deactivated hydrocarbon conversion catalyst comprising (a) one or more Lewis acids selected from the group consisting of the fluorides, chlorides and bromides of boron(III), titanium(IV), zirconium(IV), hafnium(IV), phosphorus (V), arsenic(V), tantalum(V), niobium(V), and mixtures thereof and (b) a strong Bronsted acid, may be regenerated by contacting same with hydrogen. The hydrogen reacts with the organic contaminants that deactivate the catalyst to form hydrocarbons which are more volatile and less basic, i.e. light paraffins. Preferably, a portion of the free Bronsted acid, i.e. the Bronsted acid not complexed with the catalyst contaminants, is removed from the deactivated or partially deactivated catalyst prior to and/or during contacting same with hydrogen.

When at least a portion of said deactivated or partially deactivated hydrocarbon conversion catalyst is contacted with hydrogen; e.g. a gas containing molecular hydrogen, there results, in general, a gas phase comprising light hydrocarbons and a non-gaseous phase comprising non-volatile corrosion products. The amount of Lewis acid and/or remaining Bronsted acid present in either phase is dependent upon the volatility of the particular acid components and the temperature and pressure of the regeneration zone. At least a portion of the regenerated catalyst containing one or more of the acid components may be recycled to the hydrocarbon conversion process.

DETAILED DESCRIPTION OF THE INVENTION

The hydrocarbon conversion catalyst referred to herein comprises (a) one or more Lewis acids selected from the group consisting of the fluorides, chlorides and bromides of boron(III), titanium(IV), zirconium(IV), hafnium(IV), phosphorus(V), arsenic(V), tantalum(V), niobium(V) and mixtures thereof and (b) a strong Bronsted acid. For the purposes of this invention, mixed halides (e.g. $TaF_4Cl$) may be used as a Lewis acid.

Acidic halides are preferred Lewis acids (see Olah, G.A. *Friedel-Crafts Chemistry,* John Wiley & Sons, pp. 215–216 New York, 1973). Preferred acidic halides may be selected from the group consisting of the fluorides, chlorides and bromides of titanium(IV), zirconium(IV), hafnium(IV), niobium(V), tantalum(V), and mixtures thereof. Acidic fluorides are the preferred acidic halides. Preferred acidic fluorides are titanium tetrafluoride, zirconium tetrafluoride, hafnium tetrafluoride, tantalum pentafluoride, niobium pentafluoride, or mixtures thereof. For the purpose of this invention, the pentafluoride, the pentachloride and the pentabromide of phosphorus, particularly phosphorus pentafluoride, are suitable acidic halides. When using those Lewis acids that are reduced during the hydrocarbon conversion process and/or the regeneration step (e.g., arsenic pentafluoride), it is necessary, subsequent to said reduction, to reoxidize any lower halides formed to the original Lewis acid. This may be achieved using a halogen or an interhalogen, e.g., chlorine trifluoride, or mixtures thereof. The most preferred acidic halide catalyst constituents are tantalum and niobium halides, preferably tantalum pentafluoride, niobium pentafluoride and mixtures thereof. Tantalum pentafluoride is meant to include tantalum pentafluoride as well as its complex ions, e.g., salts such as $M^I Ta_2F_{11}-$, $M^I Ta_3F_{16}-$ and the like (where $M^I$ is a univalent cation; e.g. $Na^+$), that exhibit acid properties in hydrogen fluoride and may be used as Lewis acids. This applies similarly to other acidic halides.

The second component of the catalyst system is a Bronsted acid. Suitable Bronsted acids include a hydrogen halide, trifluoroacetic acid, phosphoric acid, fluorophosphoric acids, fluorosulfonic acid, trifluoromethanesulfonic acid, methanesulfonic acid, and sulfuric acid. The preferred Brosted acid is a hydrogen halide. Useful hydrogen halides include hydrogen bromide, hydrogen chloride and hydrogen fluoride. The preferred hydrogen halide catalyst constituent is hydrogen fluoride.

The effectiveness of the catalyst is related to the molar ratio of Bronsted acid to Lewis acid. While relatively minor amounts, i.e. less than equal molar amounts, of Bronsted acid relative to Lewis acid will dissolve at least a portion of the Lewis acid and thereby effect the reaction, the rate of reaction is inordinately slow. However, the reaction rate, i.e. the yield in a given period of time, will be increased if at least an equal molar amount of Bronsted acid relative to Lewis acid is present in the reaction zone. Increasing the mole ratio of Bronsted acid to Lewis acid dissolves more of the Lewis acid and thereby provides an increasing amount of liquid phase catalyst which will favor an increased reaction rate. Thus, the mole ratio of Bronsted acid (hydrogen halide) to Lewis acid (acidic halide) is preferably at least 2:1 and more preferably at least 5:1. The favorable effects mentioned above will pass through a maximum as the Bronsted acid dilutes the acidity of the reaction system. Thus depending upon the relative amounts of catalyst constituents used, the catalyst, when no support is employed, may be a homogeneous solution of the Lewis acid or a mixture of gaseous, solid, liquid and dissolved Lewis acid in Bronsted acid.

The catalyst may be used as the neat liquid, as a diluted solution or as a liquid adsorbed on a solid support. With regard to the use of the catalyst in solution, any diluent or solvent may be used that is inert to the catalyst under the particular hydrocarbon conversion reaction conditions. Typical diluents or solvents include sulfuryl chloride fluoride, sulfuryl fluoride, sulfolanes, sulfur dioxide, mixtures thereof and the like. When a solvent or diluent is used, sufficient amounts are employed to maintain the viscosity of the reaction mixture at a desired level. The amount of diluent employed can vary appreciably and can range as high as 98 volume % of the reaction mixture. Typically, the diluent:catalyst volume ratio may range from about 20:1 to 1:10. Higher dilutions may be desirable, for example, in those reactions that proceed with high exothermicity.

Although the use of a substantially liquid phase catalyst is preferred, the catalyst system may be incorporated with a suitable solid carrier or support. Any support that is inert to the catalyst under the reaction conditions and preferably, under the regeneration conditions, may be used. The support should be pretreated, such as by heating, chemical treatment or coating to remove substantially all water and/or hydroxylic or other basic sites that might be present. Reactive supports may be rendered inert by coating them with an inert material such as aluminum trifluoride. Suitable solid supports include fluoride-treated or coated resins such as sulfonated cation exchange resins in the protonic form, fluoride treated acidic chalcites such as alumina, aluminosilicates, molecular sieves such as faujasite and zeolite, and hydrogen fluoride-resistant materials such as charcoal and halogenated polymers, e.g. Kel F, Teflon, etc.

The supported catalyst can be prepared in any suitable manner including conventional impregnation. In one embodiment, the supported catalyst is prepared by impregnating a suitable deactivated support with a Lewis acid such as tantalum pentafluoride and then with a Bronsted acid such as hydrogen fluoride.

In general, the partially deactivated catalyst may be derived from those reactions and side reactions that occur under the influence of Friedel-Craft's catalysts, e.g. isomerization, alkylation, polymerization, cracking, hydrogenation, disproportionation and the like. All of these reactions are well known to generate the same type of contaminants (see *Carbonium Ions,* Vol. II edited by George A. Olah and Paul von R. Schleyer, Wiley-Interscience, 1970, Chapter 18 by N.C. Deno, particularly page 783 wherein the author indicates that substituted allylic cations are the end product of most carbonium ion reactions in strong acid systems).

The present invention is, however, particularly applicable to isomerization and alkylation reactions. Typical isomerizable feedstocks include acyclic and alicyclic aliphatic hydrocarbons having at least four carbon atoms that are converted to a product enriched in an isomer thereof. Typically, acyclic hydrocarbons having at least four carbon atoms, that is straight chain or branched chain paraffins having from about 4 to 10 carbon atoms, preferably from about 4 to 8 carbon atoms, are converted to branched materials having higher octane ratings. Additionally, alicyclic hydrocarbons (naphthenes) having at least 6 carbon atoms, typically from 6 to about 50 carbon atoms, preferably 6 to to 15 carbon atoms, can be converted to isomers thereof by contacting the same with hydrogen in the presence of the catalyst system described previously. Mixtures of acyclic and alicyclic hydrocarbons can be used as the process feedstock. In a typical commercial operation, a paraffin stream containing mixtures of various types of open chain and closed chain paraffins is used as the process feedstock. Typical isomerization reaction conditions are summarized below:

| Range | Suitable | Preferred |
|---|---|---|
| Temperature, ° C. | 0 – 150 | 30 – 75 |
| Hydrogen Partial Pressure, atm. | 0.1 – 140 | 0.3 – 25 |
| Reaction time, min. | 0.5 – 1500 | 1 – 500 |
| Moles H$_2$/Mole Hydrocarbon | 0.01 – 2.5 | 0.1 – 1.0 |
| Space Velocity V/Hr./V | 0.05 – 200 | 0.25 – 50 |

In the alkylation of hydrocarbons with olefins, suitable olefinic starting materials are ethylene, propylene, butylenes, trimethyl ethylene and other isomeric pentenes, and similar higher monoolefinic hydrocarbons of either a straight chain or branched chain structure. Olefins containing 2 to about 12 carbon atoms per molecule are preferred while olefins containing 2 to 5 carbon atoms per molecule are particularly preferred. The reaction mixtures may also contain some amounts of diolefins. Although it is desirable from an economic viewpoint to use the normally gaseous olefins as reactants, normally liquid olefins may also be used. Thus, polymers, copolymers, interpolymers, crosspolymers, etc., of the above-mentioned olefins, as for example, propylene dimer, the diisobutylene and triisobutylene polymers, the codimer of normal and isobutylenes and the like may be used. The use of mixtures of two or more of the above-described olefins is also envisioned for this purpose.

Hydrocarbon feedstocks that are suitable for use in alkylation processes include paraffins, aromatic, alkyl substituted aromatic hydrocarbons and mixtures thereof. The paraffins as herein defined include the acyclic and alicyclic hydrocarbons. The acyclic hydrocarbons (straight and branched chain materials) contain at least 1, preferably 1 to about 12 carbon atoms per molecule, and may be exemplified by methane, ethane, propane, butanes, methylbutanes, n-pentane, methylpentanes, methylhexanes, and the like. The alicyclic hydrocarbons (naphthenes) contain at least 5, typically from 5 to about 15 carbon atoms per molecule, preferably 6 to 12 carbon atoms and may be exemplified by methylcyclopentane, dimethylcyclopentane, methylcyclohexane, ethylcyclohexane, n-pentylcyclohexane and the like. Useful aromatic and alkyl aromatic hydrocarbons contain at least 6, preferably 6 to about 20 carbon atoms per molecule and are exemplified by benzene, ethyl benzene, n-butyl benzene and the like. Other acyclic or alicyclic hydrocarbons commonly found in conventional petroleum hydrocarbon light naphtha streams and the like may be present. In addition to $iC_4$-$C_{12}$ acyclic hydrocarbons and $C_2$-$C_3$ olefins being suitable feedstocks (see U.S. Pat. No. 4,025,577 the disclosure of which is incorporated herein by reference), mixtures of $C_1$-$nC_4$ acyclic hydrocarbons can be suitable alkylated with ethylene, propylene, or mixtures thereof. Typical alkylation reaction conditions are summarized below.

| Range | Suitable | Preferred |
|---|---|---|
| Temperature, °C. | −85 − +150 | −10 − +80 |
| Hydrogen Partial Pressure, atm. | 0.1 − 100 | 0.3 − 25 |
| Reaction Time, min. | 0.001 − 60+ | 0.001 − 45 |
| Space Velocity based on olefin V/Hr./V | 0.01 − 10 | 0.04 − 5 |

As the hydrocarbon conversion reaction proceeds the activity of the catalyst system will decline. Some portion of said system may be deactivated so as to possess essentially no activity to catalyze the hydrocarbon conversion reaction while other portions may be only partially deactivated. While not wishing to be bound by any particular theory, it is believed that the present hydrocarbon conversion catalyst is deactivated or neutralized by contaminants which may be present in the hydrocarbon feedstock or which may be formed in situ during the hydrocarbon conversion reaction. The contaminants form complexes with the Lewis and/or Bronsted acid components of the catalyst system. The complexes are less catalytically active than the Bronsted/Lewis acid complexes of the catalyst system. The complexes formed with the contaminants are substantially insoluble in the hydrocarbon phase and thus accumulate in the catalyst phase. As the complexes accumulate, the acidity of the catalyst is diminished, thereby decreasing the reactivity of the catalyst system.

Both organic and inorganic contaminants can cause reduced activity of the present hydrocarbon conversion catalyst. Examples of inorganic materials that can cause the reduced activity are water, which may enter the reaction zone of the hydrocarbon conversion process in the feedstock or as the result of an operational mishap, and metal compounds which result from corrosion of the reaction zone internals or are present in heavier feedstocks. Examples of organic materials that can cause reduced activity are stable unsaturated ions, e.g. allylic ions, formed in situ during the hydrocarbon conversion reaction, organo-nitrogen, oxygen and sulfur compounds and the like. Thus, it would be desirable that said feedstock, diluents and individual catalyst consituents should be purified prior to use in the hydrocarbon conversion process to remove substantially all of the aforementioned contaminants in order to obtain maximum catalyst activity and catalyst life. By substantially is meant that the mole ratio of contaminants to Lewis acid is less than 1:2, preferably less than 1:4, and more preferably less than 1:10.

The level of activity at which the catalyst should be regenerated is not only a matter of ability to catalyze the reaction but also a matter of economics. For example, it may be desirable to regenerate a mildly deactivated catalyst to essentially fresh catalyst activity rather than allow the catalyst to be reduced to a much lower level of activity and be regenerated to fresh or to less than fresh activity. As used herein, the term "regeneration" or "regenerated" means recovering a catalyst that possesses a greater activity for hydrocarbon conversion than that possessed by the deactivated or partially deactivated catalyst. It should be understood that the regeneration process of the present invention is applicable to catalysts such as those defined above which have lost some degree of activity and that the regeneration may only partially restore the lost activity.

Although not necessary to the practice of the present invention, it may be desirable for economic reasons to separate at least a portion of the deactivated or partially deactivated catalyst from the hydrocarbon phase prior to regeneration. Preferably, substantially all of the hydrocarbon phase, i.e. all but that portion dissolved or otherwise entrained in the catalyst, is separated from the catalyst prior to regeneration. The separation may be accomplished by any suitable means including settling and decanting, volatilization and the like. Most of the entrained and/or soluble hydrocarbon remaining in the catalyst phase will be stripped therefrom during regeneration.

In the process of the present invention, the deactivated or partially deactivated hydrocarbon conversion catalyst described herein is regenerated by contact with hydrogen. The amount of hydrogen present during regeneration is not critical provided there is an amount sufficient to maintain a hydrogen partial pressure of at least 1 atmosphere and the hydrogen is effectively dispersed in the catalyst phase. The hydrogen should be present in the form of a gas containing molecular hydrogen which may be obtained from any number of sources including commercially available pure hydrogen, naphtha reformers, hydrogen plants, as well as the off-gases from any hyrotreating process. The term hydrotreating process is meant to include hydrofining, hydrocracking, hydrodesulfurization and the like or synthetic schemes in which hydrogen is a product. The hydrogen-containing gas may be pure or contain other gaseous materials such as light hydrocarbons ($C_1$-$C_{10}$), carbon dioxide, hydrogen sulfide and the like. Preferably, the hydrogen-containing gas will be substantially free of volatile sulfur compounds, unsaturated compounds and carbon monoxide. In general, the mole % of carbon monoxide, of unsaturated compounds and of sulfur compounds in the hydrogen-containing gas relative to the Lewis acid should each be less than about 10%, more preferably less than about 5% and most preferably less than about 1%. The hydrogen-containing gas may be introduced into the regeneration zone alone or be mixed with the deactivated or partially deactivated catalyst prior to introduction into the zone. Preferably, the hydrogen-containing gas will be substantially anhydrous, i.e., less than about 3 wt. % and preferably less than about 1 wt. % water.

The hydrogen reacts with the organic contaminants and converts them to more volatile and less basic hydrocarbons. It is believed that sulfur compounds are hydrocracked to hydrogen sulfide and light hydrocarbons, oxygen compounds are cleaved to form water and that nitrogen compounds form ammonium salts. These reactions are exothermic thereby requiring that the regeneration be effected under conditions that will promote favorable temperature control.

In a preferred embodiment of the present invention, a portion, preferably a major portion, most preferably substantially all (e.g. 95% or more) of the free Bronsted acid is removed from the deactivated or partially deactivated catalyst prior to and/or during regeneration. By free Bronsted acid is meant the Bronsted acid not complexed with the catalyst contaminants. The free Bronsted acid can be removed by any convenient means available to one skilled in the art such as, for example, by stripping with hydrogen or an inert gas, by evacuation and the like.

The temperature of the regeneration zone should be maintained at as low a level as possible in order to minimize undesirable side reactions, the excessive consumption of reagents, and further degradation of the hydrocarbon conversion catalyst. Higher temperatures favor the formation of lower molecular weight hydrocarbons, e.g., $C_4$ or less, thereby consuming more hydrogen than necessary. In general, the temperature will range from about 100° to about 500° C., preferably from about 140 to about 400° C., and more preferably from about 140° to about 350° C.

The total pressure at which the regeneration is effected is not critical and will depend upon the extent of catalyst deactivation which, in turn, will depend upon the nature of the material being processed, the reaction diluent, if any, as well as other process variables. The hydrogen partial pressure should be at least one atmosphere and may range from about 1 to about 500 atmospheres, preferably from about 1 to about 100 atmospheres, and most preferably from about 1 to about 50 atmospheres. The total pressure may range from about 1 to about 700 atmospheres.

The contact time required need only be that sufficient to obtain a regenerated catalyst that possesses a greater activity for hydrocarbon conversion than that possessed by said deactivated or partially deactivated hydrocarbon conversion catalyst. Thus, the contact time may vary broadly, i.e. from a few seconds to several hours, depending on the temperature, the components of the catalyst, and other inter-related variables. Generally, the contact time will vary from 1 second to about 5 hours, preferably from 10 seconds to about 2 hours, more preferably from about 1 minute to about 30 minutes.

The deactivated or partially deactivated catalyst may be regenerated in any suitable apparatus. Contacting may be effected in batch, multiple batch, semi-continuous, or continuous operation. For example, it may be carried out in continuous contacting equipment such as simple gravity operated contactors with no mechanical agitator, mechanically agitated contactors, centrifugal contactors, or packed or unpacked towers employing countercurrent or concurrent techniques with or without mixing orifices. The contacting equipment should be of appropriate design to insure intimate contact between the catalyst, which is at least partially deactivated, and the hydrogen. Equipment most suitable for a specific application can be selected by one skilled in the art. Alloy materials such as Carpenter 20 Cb-3 steel (Alloy 20), monel, Hastelloy C, aluminum 5052, aluminum 6061, and the like may be employed. Aluminum and its alloys are preferred.

Thus, when a deactivated or partially deactivated catalyst is regenerated with a gas-containing molecular hydrogen hydrogen according to the present invention, there results a gas phase comprising light alkanes such as methane, ethane, propane, butanes, pentanes, etc., and a non-gaseous phase comprising non-volatile corrosion products formed in the regeneration zone, in the hydrocarbon conversion process or in both. At least a portion of each phase may be recycled to the hydrocarbon conversion process. The gas phase, in addition to containing light alkanes, will contain both hydrogen and Bronsted acid stripped from the catalyst by the hydrogen-containing gas during regeneration. If desired, a portion, preferably a major portion, most preferably substantially all of the free Bronsted acid may be removed from the catalyst prior to said catalyst entering the regeneration zone. The Lewis acid component of the hydrocarbon conversion catalyst may also be present in the gas phase. The amount of Bronsted and/or Lewis acid components present in the gas phase will vary depending upon the physical properties of the particular acids, i.e. volatility, as well as the temperature and pressure of the regeneration zone.

The Bronsted and/or Lewis acid components may be recovered from the gas phase by several methods that would be obvious to one skilled in the art. For example, if the acid components were tantalum pentafluoride and hydrogen fluoride and sufficient amounts of tantalum pentafluoride were present in the gas phase to justify recovery, both acid components could be condensed therefrom. Preferably at least a portion of the condensate is recycled to the hydrocarbon conversion process. At least a portion of the gas phase, with or without the Lewis and/or Bronsted acid components, may be recycled to the regeneration zone to utilize any unconverted hydrogen present in the gas. If this is done, it may be desirable to remove the alkanes present in the gas, e.g. via refrigeration, absorption, etc., to enrich the recycle stream in hydrogen.

The non-gaseous phase may be solid, liquid or a mixture thereof depending upon the type of contaminants present in the deactivated catalyst and the operating conditions of the regeneration zone. The Lewis and/or Bronsted acid components not present in the gas phase will be present in the non-gaseous phase. At least a portion of the nongaseous phase may be recycled to the hydrocarbon conversion process. Non-volatile corrosion products, e.g. iron fluoride, and any oxy-compounds, e.g. tantalum oxyfluorides, formed through hydrolysis by adventitious water may be present in homogeneous solution with the non-gaseous phase or as a separate solid phase. Preferably, the corrosion products are separated from the catalyst components therein prior to recycling the non-gaseous phase to the hydrocarbon conversion process. Any solids which are present may be separated from the liquid portion of the non-gaseous phase by suitable mechanical means such as filtration or settling. If the non-volatile corrosion products and oxyfluorides are in homogeneous solution with the Lewis and/or Bronsted acid components of the catalyst and said components are volatile, e.g., tantalum pentafluoride, the heat generated during regeneration could be sufficient to volatilize the acid component selectively, thereby effecting the simultaneous purification and separation of said acid component.

The non-gaseous phase may also contain other organic species such as higher molecular weight paraffins, e.g., $C_9$–$C_{20}$, resulting from the hydrogenation of unsaturated ions. These components do not have an adverse effect on the activity of the catalyst and, therefore, may be recycled to the hydrocarbon conversion process. It should be pointed out that there may be little if any corrosion products if said catalyst contacts a non-corrodible material such as Teflon, aluminum, and the like. Thus, when using such materials, depending upon the physical properties of the catalyst components as well as the temperature and pressure of the regeneration zone, there may be no non-gaseous residue.

The following examples are presented to further illustrate the process of the present invention and are not intended to unduly restrict the limits of the claims appended hereto.

EXAMPLE 1

A sample of deactivated catalyst was obtained as follows. Sublimed tantalum pentafluoride, (55 g, 0.2 mole) was placed into a 1 liter Stainless Steel type 316 reactor in a nitrogen-flushed dry box. After assembling and evacuating the reactor, hydrogen fluoride (55 g, 2.75 mole) was distilled into the reactor. A 250 ml. mixture of n-hexane and cyclohexane (90 wt. %:10 wt. %) was then added from a metal cylinder with applied hydrogen pressure. The reactor was heated to 50° C. and pressurized to a total pressure of about 8 atmospheres with pure i.e., molecular hydrogen. After stirring at 1000 rpm for about 1 hour, the hydrocarbon was isomerized to almost equilibrium. A sample was analyzed by gas chromatography and found to contain less than 10 mole % n-$C_6$ and greater than 40 mole % 2,2-dimethylbutane, thus indicating an active catalyst. Hydrogen was then vented from the system and the reactor and contents were allowed to stand without stirring for about 2 hours at about 50° C. The reactor was subsequently cooled to about 25° C., after which the hydrocarbon was withdrawn and replaced with a fresh charge (250 ml.) of the same feed. After heating with stirring to 50° C. for about one hour under a total pressure of about 8 atmospheres, the hydrocarbon phase was found to be less than 1% isomerized. The hydrocarbon was then withdrawn and the hydrogen fluoride was vented from the reactor. A stream of dry nitrogen was passed through the reactor to remove residual hydrogen fluoride and volatile hydrocarbons. The resulting brown oil, representing deactivated catalyst, was analyzed by combustion and found to contain 21 wt. % carbon.

A 5–8 ml sample of this oil was placed in a 128 ml Hastelloy C reactor together with a small Teflon-coated magnetic stirring bar. After assembling in dry nitrogen as above, the reactor was pressurized to about 35 atmospheres with pure dry hydrogen from a cylinder. The reactor was then heated in an oil bath to about 300° C., thus doubling the pressure to about 70 atmospheres, and stirred magnetically for an hour. After cooling to about 25° C., a gas sample was removed and subjected to gas chromatographic analysis. The sample was found to contain substantial amounts, i.e. about 50 mole %, of methane and ethane but almost no propane or higher alkanes. The gases were vented and the reactor recharged with hydrogen at 20° C. and the above procedure repeated several times until the gas analysis showed that less than 5 mole % light hydrocarbons were present. The reactor, when opened at room temperature, was found to contain a black tar on the bottom and a white sublimate on the upper walls. When analyzed, the black tar was found to contain 5.1 wt. % carbon and 1.1 wt. % hydrogen and the white sublimate to contain 0.34 wt. % carbon.

This example shows that the carbon content of a catalyst that possesses little activity for hydrocarbon conversion may be reduced by at least 75% by contact with hydrogen at elevated temperature and pressure.

EXAMPLE II

A deactivated catalyst was prepared as in Example I and found to contain 19.5 wt. % carbon. About 0.5 cc of this material was placed into the 128 ml reactor so as to form a pool about 2–3 mm deep around the Teflon-coated magnetic stirrer. After assembling in a dry nitrogen atmosphere, the reactor was pressurized to 50 atmospheres total pressure with pure hydrogen. The reactor and contents were then heated at 150° C. for 15 hours. This caused the pressure to rise to about 62 atmospheres. On cooling the reactor to room temperature, a small sample of gas was analyzed and found to contain less than 1 mole % light hydrocarbons, principally propane, butanes and pentanes.

The reactor was then heated to 200° C. at which temperature the total pressure rose to about 70 atmospheres. After stirring under these conditions for one hour, the reactor was cooled. Gas chromatographic analysis showed the gas to contain 9 mole % of light alkanes, principally propane and butane with lesser amounts of ethane and methane. The reactor was vented to atmospheric pressure, refilled with hydrogen at about 35 atmospheres and heated to 300° C. at which temperature the pressure was about 70 atmospheres. After another hour, the vessel was cooled to room temperature. Analysis showed the gas to contain about 10 mole % $C_1$–$C_4$ alkanes. On opening the reactor in a dry nitrogen atmosphere, a pale yellow powder was found to be essentially free of tars. The powder was analyzed and found to contain 0.25 wt. % carbon, 1.06 wt. % nickel and 0.31 wt. % chromium. To this powder was added about 20 ml of n-hexane/cyclohexane feed. The reactor was then assembled, cooled in dry ice and evacuated. About 5 grams of hydrogen fluoride were then distilled into the vessel which was then heated to 50° C. and stirred magnetically at 500 rpm. After one hour the hydrocarbon was analyzed by gas chromatography and found to be about 20% isomerized.

This example shows that a catalyst possessing essentially no activity to hydrocarbon conversion can be substantially (98.7%) purified from organic poisons by contact with hydrogen at 300° C. and 70 atmospheres to give an active isomerization catalyst. Furthermore, this example shows that the rate of conversion of hydrogen to hydrocarbons is slow below 150° C., acceptable at 200° C. and substantially complete at 300° C. In conjunction with Example I, Example II shows that the use of a smaller amount of deactivated catalyst gives more complete removal of carbon. This is attributed to better contacting between the catalyst and the hydrogen since, as shown in Example III below, a hydrogen partial pressure of 30 atmospheres is sufficient for good carbon removal.

EXAMPLE III

A deactivated catalyst was prepared as in Example I except that reactor contents were allowed to stand at 50° C. without hydrogen for about one hour. The catalyst was then evaporated to an oil by dry nitrogen and when analyzed was found to contain 16.2 wt. % carbon and 2.17 wt. % hydrogen. 19.9 g. of this material was placed in a 300 ml stainless steel type 316 reactor in a dry nitrogen atmosphere. This reactor was charged with pure hydrogen to 35 atmospheres, a pressure that was maintained during the course of the reaction by a back-pressure regulator. With a flow of hydrogen of about 60 ml/min., the reactor was gradually heated. There were no hydrocarbons detectable in the gas issuing from the back-pressure regulator before the temperature reached 150° C. After 4 hours the temperature reached 200° C. The product gas was analyzed and found to contain 13 mole % hydrocarbons. This corresponded to a hydrogen partial pressure of about 30 atmospheres at 200° C. After several hours at this temperature and hydrogen flow rate, the hydrocarbon in the product gas had reached very low levels, i.e. less than 0.3 mole %. The temperature was raised to 250° and then 275° C., but the conversion to alkanes, principally methane and ethane, did not exceed 0.2 mole %. After cooling to room temperature and venting the gases, the reactor was opened in dry nitrogen and the pale yellow crystalline product was removed for analysis. It was found to contain 0.55 wt. % carbon which corresponded to 96.7% removal of organic impurities.

This example shows that carbon can be substantially removed from a deactivated catalyst containing hydrogen fluoride and tantalum pentafluoride at temperatures below 275° C. and at hydrogen partial pressures no greater than about 30 atmospheres. It also shows that up to 13 mole % of alkanes in the gas stream has no adverse affect on the reaction.

EXAMPLE IV

About 20 grams of the deactivated catalyst from Example III was placed into the reactor as before and pressurized to about 16 atmospheres with hydrogen. The temperature of the reactor was raised to 100° C. for 3½ hours at a hydrogen flow rate of about 30 cc/min. At this temperature, the production of light hydrocarbons was low, i.e. 0.2 mole %, and comprised predominantly butanes. After raising the temperature to 150° C., the alkanes soon comprised about 1.2 mole % of the product gases, still primarily butanes. After increasing the temperature to 175° C., the product gas was analyzed and found to contain about 5.7 mole % light hydrocarbons as shown below:

| $CH_4$ | 1.1% |
|---|---|
| $C_2H_6$ | 0.7% |
| $C_3H_8$ | 1.9% |
| $C_4H_{10}$ | 1.7% |
| $C_5H_{12}$ | 0.3% |
| $C_6H_{14}$ | 0.01% |

After the conversion of hydrogen to hydrocarbon had decreased, the temperature was raised to 200° C. which increased the conversion to about 4 mole %. The conversion then dropped to 1 mole % at which time the temperature was raised to 250° C. At this temperature, a maximum of 2.5 mole % light hydrocarbons was produced. When the conversion dropped to 0.8 mole %, the reactor was cooled and vented. The product was a light brown-colored residue that contained 0.91% carbon.

The example shows that more than 95% of the carbon in a deactivated catalyst can be removed by contact with hydrogen at a temperature less than 250° C. and at total pressures of about 17 atmospheres, of which no more than 15 atmospheres need be hydrogen.

EXAMPLE V

Into a 128 ml Hastelloy C reactor containing a Teflon coated stirrer were placed (in a dry nitrogen atmosphere) tantalum pentafluoride (16 g; 0.058 mole) and ethylbenzene (1.39 g; 0.013 mole). The reactor was assembled and cooled in a bath at −78° C. After evacuation, anhydrous hydrogen fluoride (19.7 g; 0.985 mole) was distilled in. The ethylbenzene becomes protonated by the acid and behaves as a poisonous base to the catalyst. After warming to room temperature, the vessel was charged with pure hydrogen to a pressure of 300 psig. The vessel was then placed in a heating bath at 125° C. for 3 hours while the contents were stirred magnetically. After this treatment, the vessel was cooled in ice and 2.3 liters of gas were recovered. Analysis by gas chromatography indicated that the gas contained the following:

| Methane | 6.6 | vol. % |
|---|---|---|
| Ethane | 1.66 | vol. % |
| Propane | 0.13 | vol. % |
| Butanes | 0.029 | vol. % |

This corresponds to the conversion of 9.27% of the original ethylbenzene into light gaseous products.

EXAMPLE VI

Example V was repeated using ethylbenzene (0.041 mole) and tantalum pentafluoride (0.0135 mole), i.e. in a similar ratio, but only about half the amount of hydrogen fluoride (11.3 g. 0.595 moles).

After pressuring to 300 psig with pure hydrogen and heating at 125° C. for 3 hours, the bomb was cooled in ice. 2.13 liters of gas having the following composition were recovered.

| Methane | 10.4 | vol. % |
|---|---|---|
| Ethane | 3.63 | vol. % |
| Propane | 0.31 | vol. % |
| Butanes | 0.01 | vol. % |

This corresponds to the conversion of 15% of the original ethylbenzene to light gaseous products.

EXAMPLE VII

Example V was repeated using substantially the same amounts of ethylbenzene (0.059 mole) and tantalum pentafluoride (0.0121 mole). To these was added anhydrous hydrogen fluoride (6.7 g. 0.335 mole) and the mixture stirred for ten minutes to effect solution of the ethylbenzene. The vessel was then cooled to 0° C. and the bulk of the hydrogen fluoride removed by evacuation on a metal vacuum line. By this method, the weight of hydrogen fluoride left in the reactor was reduced to 0.5 g.

The vessel was then charged with 300 psig of pure hydrogen as before and heated at 125° C. for 3 hours. After cooling in ice, the gas was analyzed as before. 2.3 liters of gas having the following composition were recovered:

| Methane | 12 | vol. % |
|---|---|---|
| Ethane | 7 | vol. % |
| Propane | 3.5 | vol. % |
| Butanes | 0.4 | vol. % |

This corresponds to the conversion of 36.7% of the ethylbenzene into light gaseous products.

As shown in the table below, Examples V-VII illustrate that regeneration of the catalyst becomes easier as increasing amounts of Bronsted acid are removed therefrom before and/or during regeneration.

| Example | Molar Ratios | | | Conversion of Ethylbenzene to Gases |
|---------|------|--------|--------------|-------|
|         | HF   | TaF$_5$ | Ethylbenzene |       |
| V       | 75   | 4.39   | 1            | 9.27  |
| VI      | 14.5 | 3.04   | 1            | 15.0  |
| VII     | 2.1  | 4.45   | 1            | 36.7  |

EXAMPLE VIII

Into an aluminum lined autoclave equipped with aluminum dip legs and turbines was placed tantalum pentafluoride (55.2 g) in a dry nitrogen atmosphere. The reactor was assembled and anhydrous hydrogen fluoride (50.2 g) was added from a steel bomb under hydrogen pressure, followed by 250 mls. of a mixed $C_5-C_6$ paraffin feed. The reactor and contents were heated to 50° C. and the total pressure adjusted to 100 psig with pure hydrogen. The contents were stirred at 1000 rpm and a small sample of the hydrocarbon was removed periodically for analysis by gas chromatography. The pseudo-first order rate constant describing the conversion of normal hexane into its isomers was found to be 3.5 hours$^{-1}$.

The catalyst was then allowed to remain in contact with the hydrocarbon at 60° C. with no stirring and at a low hydrogen partial pressure of about 10 psi for one hour. The hydrocarbon layer was then removed and replaced by a fresh charge of 250 mls of the same hydrocarbon feed. An isomerization was conducted under the same conditions as those used before, i.e. 50° C., a total pressure of 100 psig and stirring at 1000 rpm. The pseudo first order rate constant which described the rate of conversion of normal hexane into its isomers was then found to be 1.0 hr.$^{-1}$, which indicated that the catalyst was about 72% deactivated.

All of the hydrocarbon that could be removed through the dip leg was discharged, leaving a few milliliters on top of the acid phase. The hydrogen fluoride was vented as a gas through an outlet in the top of the reactor and the residue in the reactor was stripped with a stream of pure hydrogen until there was very little hydrogen fluoride left in the residue. When the gases issuing through the outlet ceased to fume appreciably in contact with moist air, the vent was closed and the pressure brought to 300 psig with pure hydrogen gas. The temperature of the reactor was gradually raised to 250° C. while a stream of hydrogen passed through the reactor and out through a ½ inch aluminum air-cooled reflux condenser. The pressure in the reactor was maintained at 300 psi by means of a back pressure regulator. The gases issuing from the system were analyzed by gas chromatography, and found to contain light paraffins in the range $C_1-C_5$.

As time proceeded and the temperature increased, both the concentration and distribution of these gases changed, reaching a maximum of 35.7 mole % of which methane comprises approximately half at 250° C. After several hours the concentration of those gases began to decline. After five hours, when 28.1 liters (measured under atmospheric conditions) had been passed, the light paraffins comprised less than 14% of the effluent gases.

The reactor was then cooled to 25° C. and vented to atmospheric pressure. Anhydrous hydrogen fluoride (58 g.) was added under hydrogen pressure and the reactor was warmed to 42° C. The hydrogen was vented through the air cooled condenser and the HF was refluxed for about 30 minutes to wash all the tantalum pentafluoride into the bottom of the reactor. Excess hydrogen fluoride (8 g.) was then vented from the reactor leaving, as near as could be determined, the same amount of hydrogen fluoride as in the initial test of activity.

To the reactor was then added 250 ml. of the same hydrocarbon feed as before. An isomerization was conducted under the same conditions as before and the pseudo-first order rate constant, which describes the rate at which normal hexane was found to convert to its isomers, was found to be 3.5 hrs.$^{-1}$.

This example shows that the catalyst, which upon partial deactivation had lost about 72% of its activity, was thus restored fully to its original activity.

Thus it is desirable that the molar ratio of hydrogen halide to Lewis acid be maintained below about 100:1 (i.e., between 1:1 and about 100:1), preferably between 1:1 and about 75:1, more preferably between 2:1 and about 75:1, and most preferably between 5:1 and about 50:1.

What is claimed is:

1. In a hydrocarbon conversion process which comprises contacting a hydrocarbon feedstock with a substantially liquid phase catalyst comprising (a) one or more Lewis acids selected from the group consisting of the fluorides, chlorides and bromides of tantalum(V), niobium(V) and mixtures thereof and at least an equal molar amount of (b) a strong Bronsted acid, thereby forming a hydrocarbon phase and a catalyst phase, said catalyst phase having become at least partially deactivated due to the formation of catalytically less active complexes with at least a portion of said Lewis acid, the improvement which comprises recovering at least a portion of the Lewis acid component of said catalyst by contact with hydrogen at a temperature between about 100° and about 500° C. and at a hydrogen partial pressure of at least 1 atmosphere for a period of time sufficient to obtain the Lewis acid component of said catalyst possessing a lower level of said catalytically less active complexes than that possessed by the Lewis acid component of said partially deactivated catalyst.

2. The process of claim 1 wherein said Bronsted acid is a hydrogen halide selected from the group consisting of hydrogen fluoride, hydrogen chloride, and hydrogen bromide.

3. The process of claim 1 wherein at least a portion of said Bronsted acid is separated from the catalyst phase prior to said recovery.

4. The process of claim 3 wherein at least a portion of the Lewis acid component of the catalyst phase thus recovered is recycled to said hydrocarbon conversion process.

5. The process of claim 1 wherein at least a portion of said Bronsted acid is separated from the catalyst phase during said recovery.

6. The process of claim 5 wherein at least a portion of the Bronsted acid thus recovered is recycled to the hydrocarbon conversion process.

7. The process of claim 1 wherein the Bronsted acid is hydrogen fluoride, hydrogen chloride, hydrogen bromide, fluorosulfonic acid, trifluoromethanesulfuric acid, or methanesulfonic acid.

8. In a hydrocarbon conversion process which comprises contacting a hydrocarbon feedstock with a substantially liquid phase catalyst comprising a metal fluoride selected from the group consisting of tantalum pentafluoride, niobium pentafluoride and mixtures thereof in combination with at least an equal molar amount of hydrogen fluoride, thereby forming a hydrocarbon phase and a catalyst phase, said catalyst phase having become at least partially deactivated due to the formation of catalytically less active complexes with at least a portion of said metal fluoride, the improvement which comprises recovering at least a portion of the metal fluoride component of said catalyst by contact with hydrogen at a temperature in the range of from about 100° to about 500° C. and at a hydrogen partial pressure of at least 1 atmosphere for a period of time sufficient to obtain the metal fluoride component of said catalyst possessing a lower level of said catalytically less active complexes than that possessed by the metal fluoride component of said partially deactivated catalyst.

9. The process of claim 8 wherein at least a portion of said hydrogen fluoride is separated from said catalyst phase prior to said recovery.

10. The process of claim 9 wherein at least a portion of the metal fluoride component of the catalyst thus recovered is recycled to said hydrocarbon conversion process.

11. The process of claim 8 wherein at least a portion of said hydrogen fluoride is separated from said catalyst phase during said recovery.

12. The process of claim 11 wherein at least a portion of the catalyst components thus recovered are recycled to the hydrocarbon conversion process.

13. The process of claim 8 wherein said recovery is effected at a hydrogen partial pressure ranging between about 1 to about 500 atmospheres and at a temperature ranging from about 140° to about 400° C.

14. In an isomerization process which comprises contacting a feedstock containing a component selected from the group consisting of acyclic hydrocarbons having at least four carbon atoms, alicyclic hydrocarbons having at least six carbon atoms and mixtures thereof, with a substantially liquid phase catalyst comprising a metal fluoride selected from the group consisting of tantalum pentafluoride, niobium pentafluoride and mixtures thereof in combination with at least an equal molar amount of hydrogen fluoride, thereby forming a hydrocarbon phase andd a catalyst phase, said catalyst phase having become at least partially deactivated due to the formation of catalytically less active complexes with at least a portion of said metal fluoride, the improvement which comprises recovering at least a portion of the metal fluoride component of said catalyst by contact with hydrogen at a temperature in the range of from about 100° to about 500° C. and at a hydrogen partial pressure in the range of from about 1 to about 500 atmospheres for a period of time sufficient to obtain the metal fluoride component of said catalyst possessing a lower level of said catalytically less active complexes than that possessed by the metal fluoride component of the partially deactivated catalyst.

15. The process of claim 14 wherein at least a portion of said hydrogen fluoride is separated from said catalyst phase prior to said recovery.

16. The process of claim 15 wherein at least a portion of the metal fluoride component of the catalyst thus recovered is recycled to said hydrocarbon conversion process.

17. The process of claim 14 wherein at least a portion of said hydrogen fluoride is separated from said catalyst phase during said recovery.

18. The process of claim 17 wherein at least a portion of the catalyst components thus recovered are recycled to the hydrocarbon conversion process.

19. The process of claim 14 wherein said recovery is effected at a hydrogen partial pressure between about 1 and about 100 atmospheres and at a temperature between about 140° and 400° C.

20. In an alkylation process which comprises contacting a feedstock containing a component selected from the group consisting of acyclic hydrocarbons having at least one carbon atom, alicyclic hydrocarbons having at least 5 carbon atoms, aromatic hydrocarbons, alkyl aromatic hydrocarbons and mixtures thereof, and olefins containing from 2 to about 12 carbon atoms per molecule, with a substantially liquid phase catalyst comprising a metal fluoride selected from the group consisting of tantalum pentafluoride, niobium pentafluoride and or mixtures thereof, in combination with at least an equal molar amount of hydrogen fluoride, thereby forming a hydrocarbon phase and a catalyst phase, said catalyst having become at least partially deactivated due to the formation of catalytically less active complexes with at least a portion of said metal fluoride, the improvement which comprises recovering at least a portion of the metal fluoride component of said catalyst by contact with hydrogen at a temperature in the range of from about 100° to about 500° C. and at a hydrogen partial presure in the range of from about 1 to about 500 atmospheres for a period of time sufficient to obtain a catalyst possessing a lower level of said catalytically less active complexes than that possessed by the metal fluoride component of the partially deactivated catalyst.

21. The process of claim 20 wherein at least a portion of said hydrogen fluoride is separated from said catalyst phase prior to said recovery.

22. The process of claim 21 wherein at least a portion of the metal fluoride component of the catalyst thus recovered is recycled to said hydrocarbon conversion process.

23. The process of claim 20 wherein at least a portion of said hydrogen fluoride is separated from said catalyst phase during said recovery.

24. The process of claim 23 wherein at least a portion of the catalyst components thus recovered are recycled to the hydrocarbon conversion process.

25. The process of claim 20 wherein said recovery is effected at a hydrogen partial pressure between about 1 and about 100 atmospheres and at a temperature between about 140° and 400° C.

26. The process of claim 20 wherein a feedstock containing $iC_4$-$C_{12}$ acyclic hydrocarbons is alkylated with $C_2$-$C_8$ olefins.

27. The process of claim 20 wherein a feedstock comprising a component selected from the group consisting of methane, ethane, propane, n-butane and mixtures thereof is alkylated with an olefin selected from the group consisting of ethylene, propylene and mixtures thereof.

* * * * *